(12) United States Patent
Rogers

(10) Patent No.: US 10,835,667 B1
(45) Date of Patent: Nov. 17, 2020

(54) IV COMFORT AND SAFETY ASSIST DEVICE AND METHOD

(71) Applicant: M. Maurice Rogers, Downsville, LA (US)

(72) Inventor: M. Maurice Rogers, Downsville, LA (US)

( * ) Notice: Subject to any disclaimer, the term of this patent is extended or adjusted under 35 U.S.C. 154(b) by 16 days.

(21) Appl. No.: 16/672,958

(22) Filed: Nov. 4, 2019

(51) Int. Cl.
*A61M 5/14* (2006.01)

(52) U.S. Cl.
CPC ........ *A61M 5/1418* (2013.01); *A61M 5/1415* (2013.01); *A61M 5/1417* (2013.01); *A61M 2205/0216* (2013.01); *A61M 2209/082* (2013.01); *A61M 2209/084* (2013.01)

(58) Field of Classification Search
CPC .............. A61M 5/1415; A61M 5/1417; A61M 5/1418; A61M 2205/0216; A61M 2205/0238; A61M 2209/082; A61M 2209/084
See application file for complete search history.

(56) References Cited

U.S. PATENT DOCUMENTS

| | | | |
|---|---|---|---|
| 4,666,111 A * | 5/1987 | Schuler ............... | A61M 5/1415 248/125.1 |
| 4,690,674 A | 9/1987 | Dalglish | |
| 5,709,665 A * | 1/1998 | Vergano ............... | A61M 5/1418 604/174 |
| 7,766,289 B2 | 8/2010 | Newkirk et al. | |
| 9,486,374 B2 | 11/2016 | Heimbrock et al. | |
| 9,931,258 B2 | 4/2018 | Heimbrock et al. | |

* cited by examiner

*Primary Examiner* — Shefali D Patel
(74) *Attorney, Agent, or Firm* — R. Keith Harrison

(57) ABSTRACT

An intravenous fluid administration comfort and safety assist method may include deploying an intravenous fluid administration stand adjacent to a patient bed; suspending an intravenous fluid administration container on the intravenous fluid administration stand, the intravenous fluid administration container having an intravenous fluid administration line; obtaining an intravenous fluid administration comfort and safety assist device including a restraining member having a proximal restraining member end, a distal restraining member end and a line attachment member on the distal restraining member end, the distal restraining member end and the proximal restraining member end disposed within a common straight line; attaching the proximal restraining member end of the restraining member to the intravenous fluid administration stand; attaching the line attachment member on the distal restraining member end of the restraining member to the intravenous fluid administration line; and inserting the intravenous fluid administration line in a patient. An intravenous fluid administration line restraining assembly is also disclosed.

20 Claims, 7 Drawing Sheets

IV COMFORT AND SAFETY ASSIST DEVICE AND METHOD

FIELD

Illustrative embodiments of the disclosure relate to intravenous fluid administration devices (IVs). More particularly, illustrative embodiments of the disclosure relate to an IV comfort and safety assist device and method which restrains and maintains an IV line in a configuration or position for optimum comfort and safety of a patient.

BACKGROUND

The background description provided herein is solely for the purpose of generally presenting the context of the illustrative embodiments of the disclosure. Aspects of the background description are neither expressly nor impliedly admitted as prior art against the claimed subject matter.

A typical conventional intravenous fluid administration (IV) stand may include a vertical stand shaft which extends from a wheeled stand base. An elongated stand arm may be supported on the stand shaft. A supply bag, bottle or other IV container filled with transfusion blood, saline solution, liquid medication and/or other liquid which is to be intravenously administered to a patient may be suspended from the stand arm. An IV line may be attached to the IV container. A cannulated needle may terminate the IV line for insertion into a vein in the patient's arm.

One of the difficulties which is frequently encountered in the use of conventional IV stands is that the tubular IV line typically has a slack configuration as it trails from the container on the IV stand to the patient. This may cause the IV line to touch the floor next to the bed of the patient. Consequently, the IV line may be vulnerable to being crimped or stepped on, kicked or moved by medical personnel or by persons who visit the patient. Moreover, the IV line may be inadvertently caught in the bed covers, railings or other portions of the patient's bed, interfering with movement and comfort of the patient as the patient lies in the bed.

Accordingly, an IV comfort and safety assist device and method which restrains and maintains an IV line in a configuration or position for optimum comfort and safety of a patient may be desirable.

SUMMARY

Illustrative embodiments of the disclosure are generally directed to an intravenous fluid administration comfort and safety assist method. An illustrative embodiment of the method may include deploying an intravenous fluid administration stand adjacent to a patient bed; suspending an intravenous fluid administration container on the intravenous fluid administration stand, the intravenous fluid administration container having an intravenous fluid administration line; obtaining an intravenous fluid administration comfort and safety assist device including a restraining member having a proximal restraining member end, a distal restraining member end and a line attachment member on the distal restraining member end, the distal restraining member end and the proximal restraining member end disposed within a common straight line; attaching the proximal restraining member end of the restraining member to the intravenous fluid administration stand; attaching the line attachment member on the distal restraining member end of the restraining member to the intravenous fluid administration line; and inserting the intravenous fluid administration line in a patient.

Illustrative embodiments of the disclosure are further generally directed to an intravenous fluid administration line restraining assembly. An illustrative embodiment of the assembly may include an intravenous fluid administration stand including a stand shaft and at least one stand arm carried by the stand shaft. An intravenous fluid administration container may be carried by the at least one stand arm of the intravenous fluid administration stand. An intravenous fluid administration line may extend from the intravenous fluid administration container. An intravenous fluid administration comfort and safety assist device may include a restraining member having a proximal restraining member end attached to the at least one stand arm of the intravenous fluid administration stand, a distal restraining member end and a line attachment member on the distal restraining member end and attached to the intravenous fluid administration line. The distal restraining member end and the proximal restraining member end may be disposed within a common straight line.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
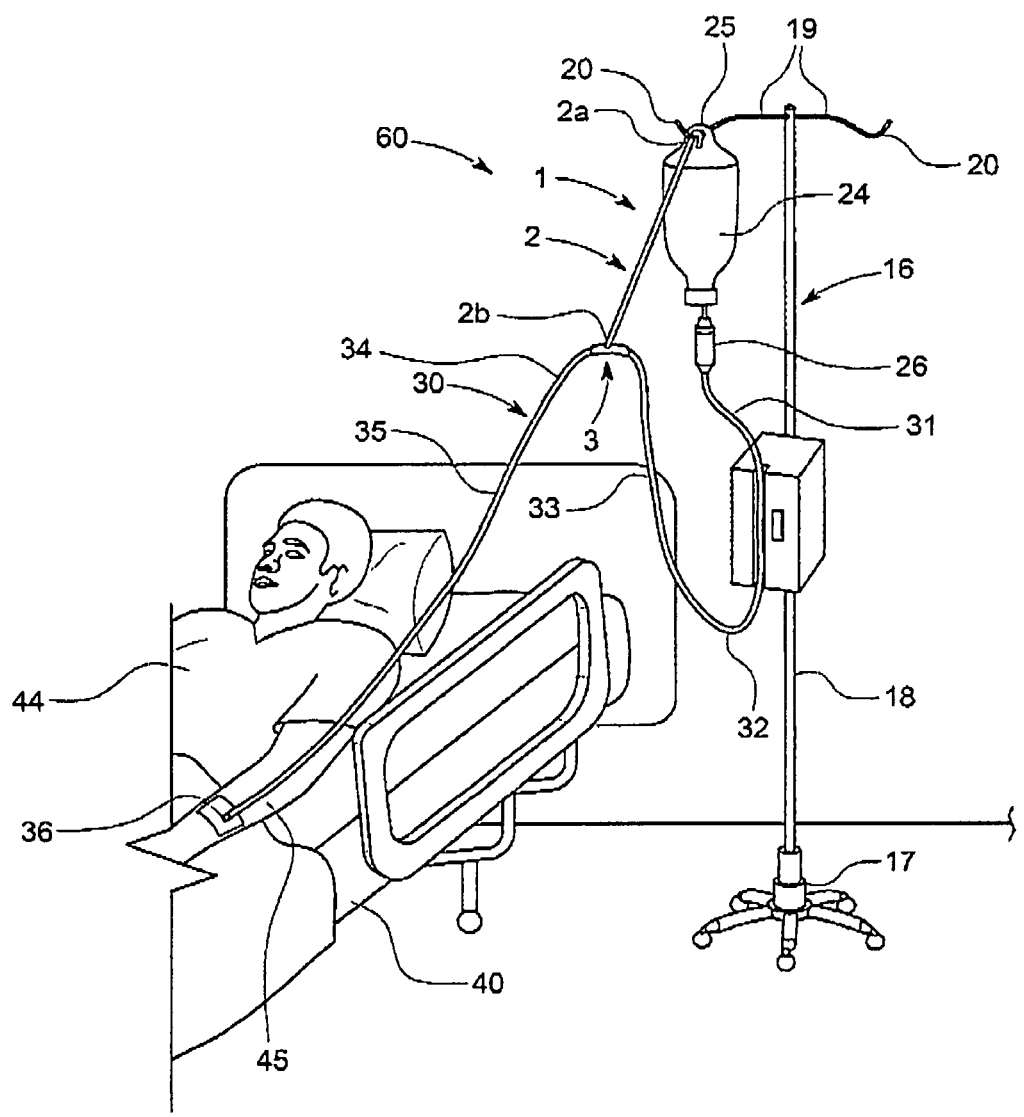
FIG. 1 is a perspective view of a typical IV stand deployed adjacent to a bed with a patient reclining in the bed, an IV container suspended from the IV stand and an IV line trailing from the IV container to the patient, with an illustrative embodiment of the IV comfort and safety assist device attached to the IV stand and to the IV line and constraining the IV line for optimum comfort and safety of the patient in typical application of the IV comfort and safety assist device.

Referring initially to FIG. 1 of the drawings, an illustrative embodiment of the intravenous comfort and safety assist device, hereinafter device, is generally indicated by reference numeral 1. As will be hereinafter described, the device 1 may be deployed as part of an IV restraining assembly 60 on an intravenous fluid administration stand, hereinafter IV stand 16, to restrain and maintain an intravenous fluid administration line, hereinafter IV line 30, in a configuration or position which facilitates optimum comfort and safety to a patient 44 typically as the patient 44 lies in a patient bed 40 next to the IV stand 16. The IV line 30 typically extends from an IV container 24 which may include a supply bag, bottle or other container filled with transfusion blood, saline solution, liquid medication and/or other liquid which is to be intravenously administered to the patient 44 through the IV line 30. Accordingly, the device 1 may prevent the IV line 30 from touching the floor next to the patient bed 40 and thus, from being inadvertently crimped, stepped on, kicked or moved by medical personnel or by persons who visit the patient 44. The device 1 may further prevent the IV line 30 from being inadvertently caught in the bed covers, railings or other portions of the patient bed 40 and interfering with movement and comfort of the patient 44 in the patient bed 40 to facilitate maximum freedom of movement of the patient 44 in the patient bed 40.

Figure 2:
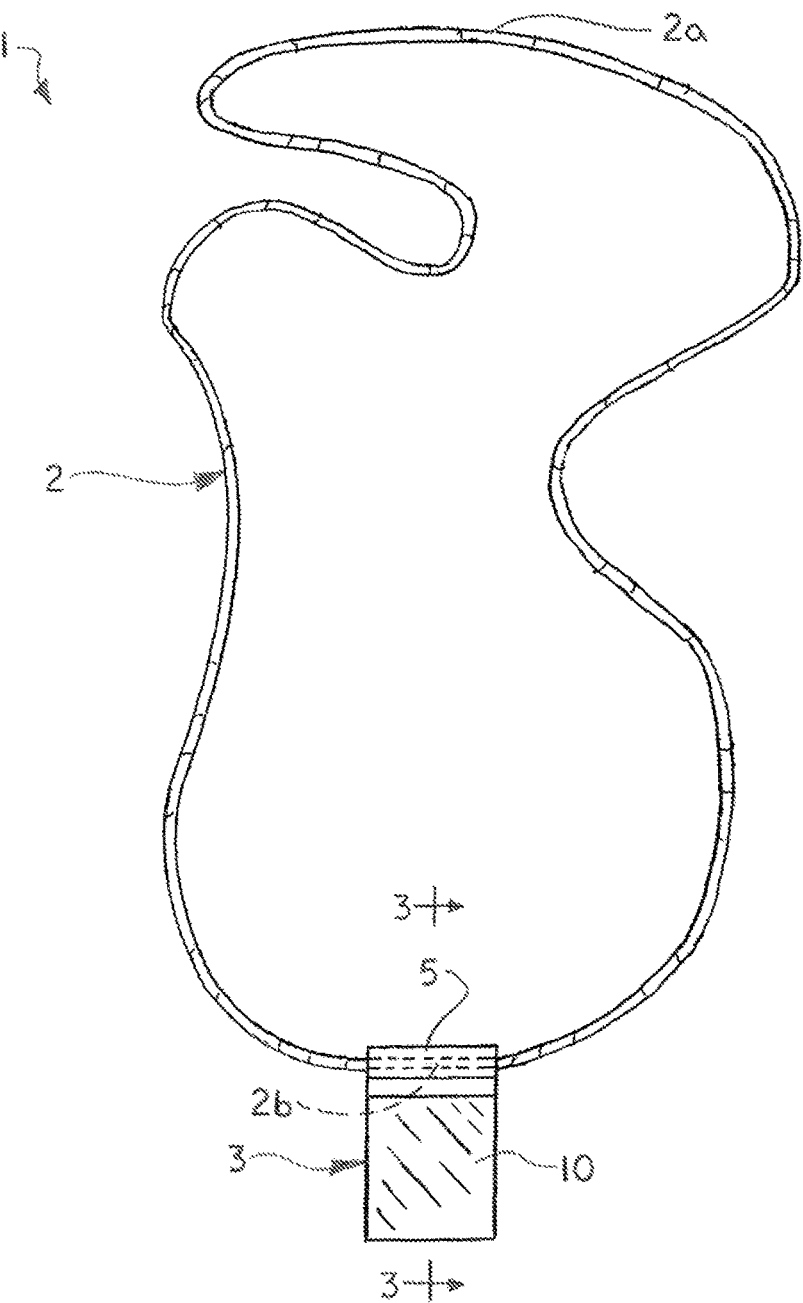
FIG. 2 is a top view of an illustrative embodiment of the IV comfort and safety assist device in a non-functional configuration.
Figure 3:
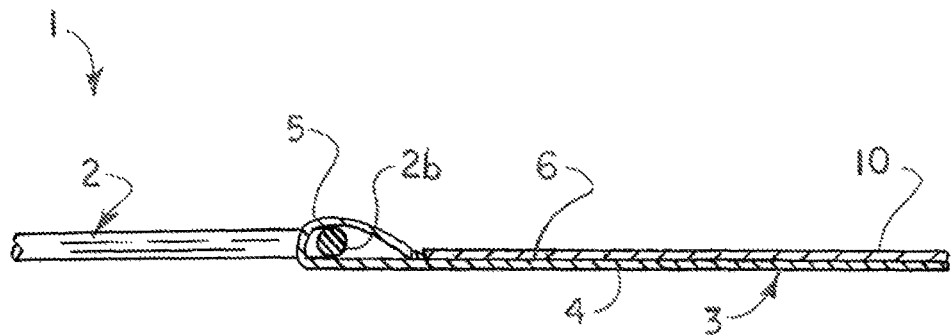
FIG. 3 is a sectional view, taken along section lines 3-3 in FIG. 2, of a typical line attachment member of the illustrative IV comfort and safety assist device.
Figure 4:
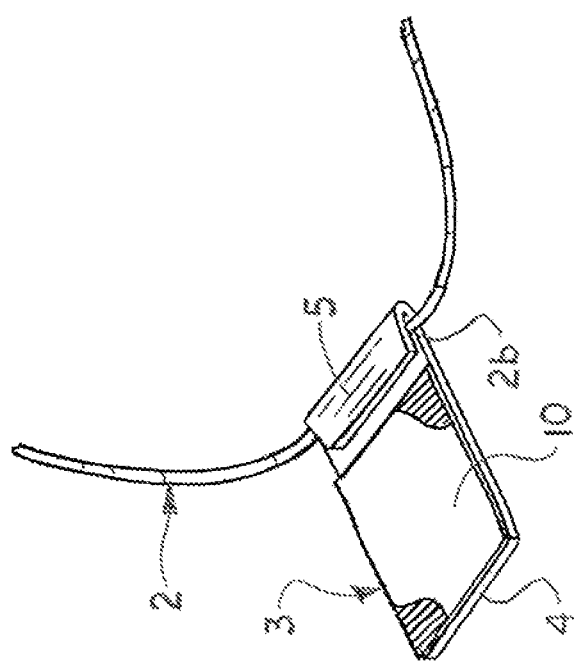
FIG. 4 is a perspective view of the line attachment member on the restraining member (partially in section) of the illustrative IV comfort and safety assist device.

Referring next to FIGS. 2-4 of the drawings, the device 1 may include a restraining member 2. The restraining member 2 may include an elongated strip, band or segment of nylon, fabric, rubber and/or other suitable material and may be flexible or elastic in some embodiments. The restraining member 2 may have a proximal restraining member end 2a and a distal restraining member end 2b. The proximal restraining member end 2a may be suitable configured for engagement with or attachment to the IV stand 16 and the distal restraining member end 2b may be configured for engagement with or attachment to the IV line 30 according to the knowledge of those skilled in the art and typically in a manner which will be hereinafter described. When deployed in the functional configuration illustrated in FIG. 1, the length of the restraining member 2, or the distance between the proximal restraining member end 2a and the distal restraining member end 2b, may be from about 12 inches to about 18 inches, and most preferably, about 15 inches.

A line attachment member 3 may be provided on the distal restraining member end 2b of the restraining member 2. The line attachment member 3 may include any type or combination of clip, clamp, fastener and/or other element or component which is suitably configured to engage the IV line 30. As illustrated in FIG. 3, in some embodiments, the line attachment member 3 may include a base layer 4. The base layer 4 may include a flexible or resilient pad or other material or combination of materials such as commercially available foam tape, fabric and paper, for example and without limitation. The base layer 4 may have an adhesive surface 6. A removable cover layer 10 may remain attached to the adhesive surface 6 prior to use. A base layer loop 5 may be formed and secured in the base layer 4. In some embodiments, the looped distal restraining member end 2b of the restraining member 2 may extend through the base layer loop 5 to attach the line attachment member 3 to the restraining member 2. In some embodiments, the device 1 may consist essentially of the restraining member 2 and the line attachment member 3.

Referring next to FIGS. 1 and 5-9 of the drawings, in typical application of the device 1, an IV stand 16 may be deployed next to a patient bed 40 in a hospital, clinic, home or other location in which a patient 44 will be subjected to medical treatment. The IV stand 16 may have a conventional design with a typically wheeled stand base 17. A stand shaft 18 may extend upwardly from the stand base 17. At least one stand arm 19 may be supported by the stand shaft 18. Each stand arm 19 may have a curved or angled arm terminus 20.

An IV container 24 which contains a supply of transfusion blood, saline solution, liquid medication and/or other liquid (not illustrated) which is to be intravenously administered to the patient 44 may be suspended from the stand arm 19 of the IV stand 16. In some applications, the IV container 24 may have a container attachment tab 25 with a tab opening (not illustrated) which receives the stand arm 19 as the IV container 24 is placed on the stand arm 19. An IV line 30 may be fitted with a drip meter 26 which is attached to the bottom of the IV container 24. A cannulated needle 36 may terminate the IV line 30 for insertion into a vein in the patient's arm 45 typically as the patient 44 reclines comfortably in the patient bed 40.

Figure 9:
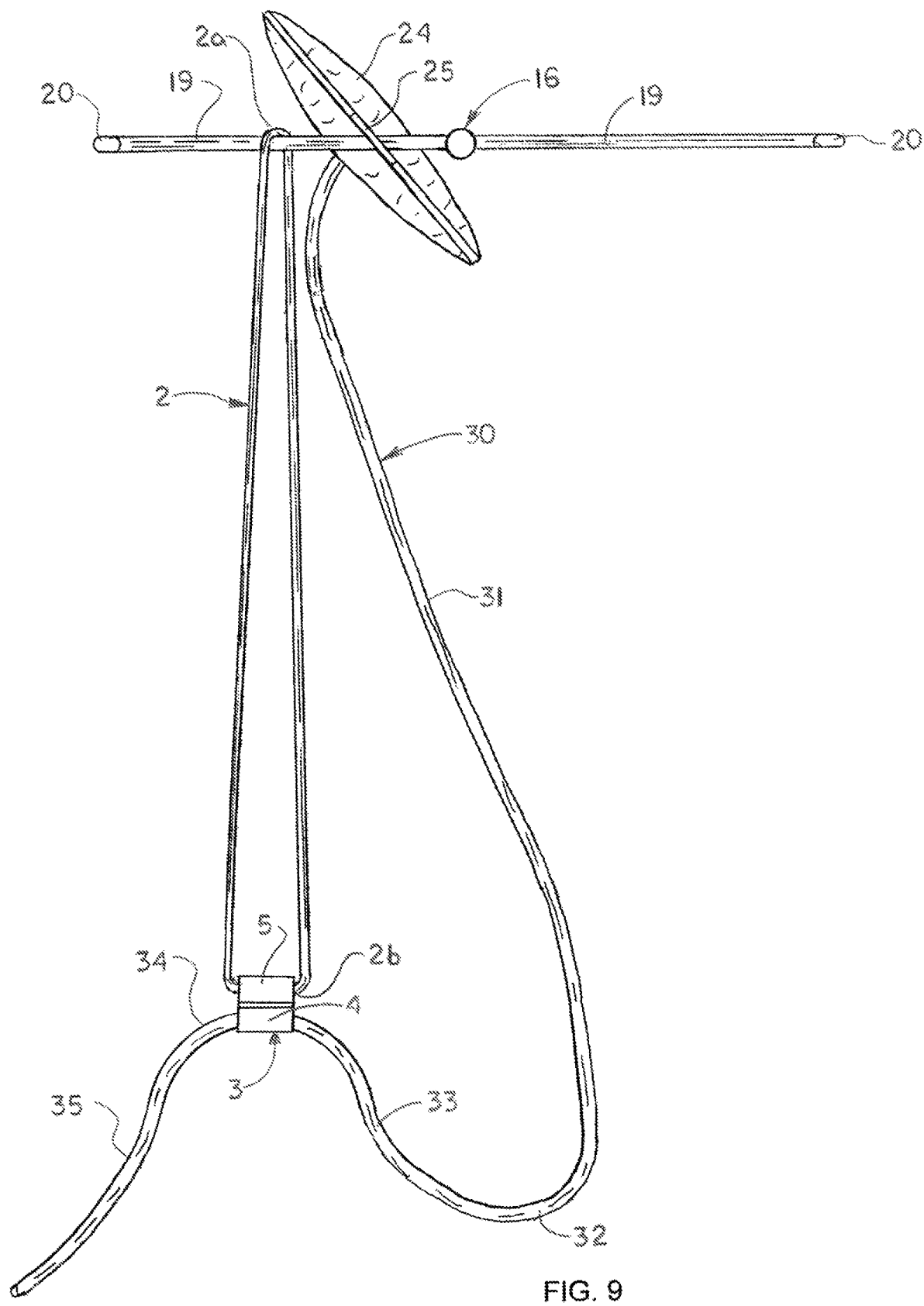
FIG. 9 is a top view of the IV stand with the IV container suspended from the IV stand and the restraining member attached to the IV stand and the IV line (partially in section) in typical application of the IV comfort and safety assist device.

The device 1 may be deployed in place by initially attaching the proximal restraining member end 2a of the restraining member 2 to the stand arm 19 of the IV stand 16. As illustrated in FIG. 9, in some embodiments, this may be accomplished by initially placing the looped proximal restraining member end 2a of the restraining member 2 over the arm terminus 20 and then sliding the proximal restraining member end 2a along the stand arm 19 until the proximal restraining member end 2a is typically disposed adjacent to the container attachment tab 25 of the IV container 24. In other embodiments, the proximal restraining member end 2a may be attached to the stand arm 19 of the IV stand 16 using alternative attachment or fastening methods or techniques known by those skilled in the art.

Figure 5:
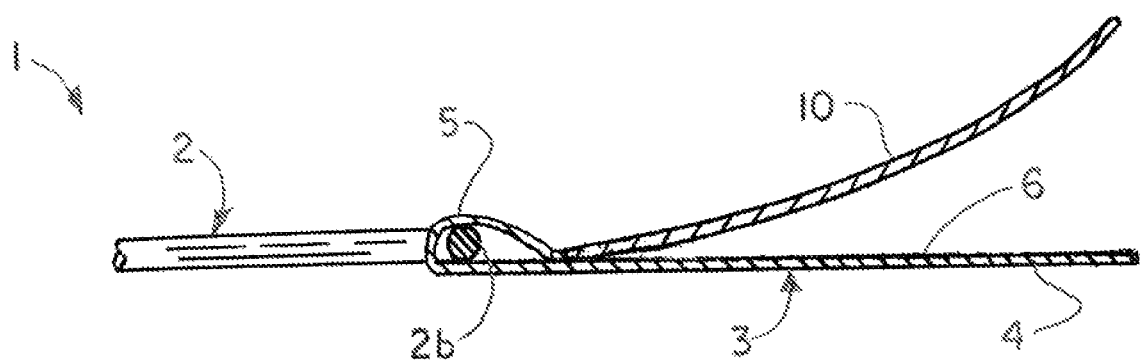
FIG. 5 is a sectional view, also taken along section lines 3-3 in FIG. 2, of the line attachment member, more particularly illustrating typical removal of a cover layer from an adhesive surface on a base layer of the line attachment member preparatory to attachment of the line attachment member to the IV line in typical application of the illustrative IV comfort and safety assist device.

The distal restraining member end 2b may next be pulled in a straight line away from the proximal restraining member end 2a of the restraining member 2 until the restraining member 2 is disposed in a taut configuration and the distal restraining member end 2b and the proximal restraining member end 2a are disposed within a common straight line. The line attachment member 3 may be held in position for subsequent attachment of the IV line 30 to the line attachment member 3. As illustrated in FIG. 5, the cover layer 10 may be detached from the adhesive surface 6 on the line attachment member 3.

Figure 6:
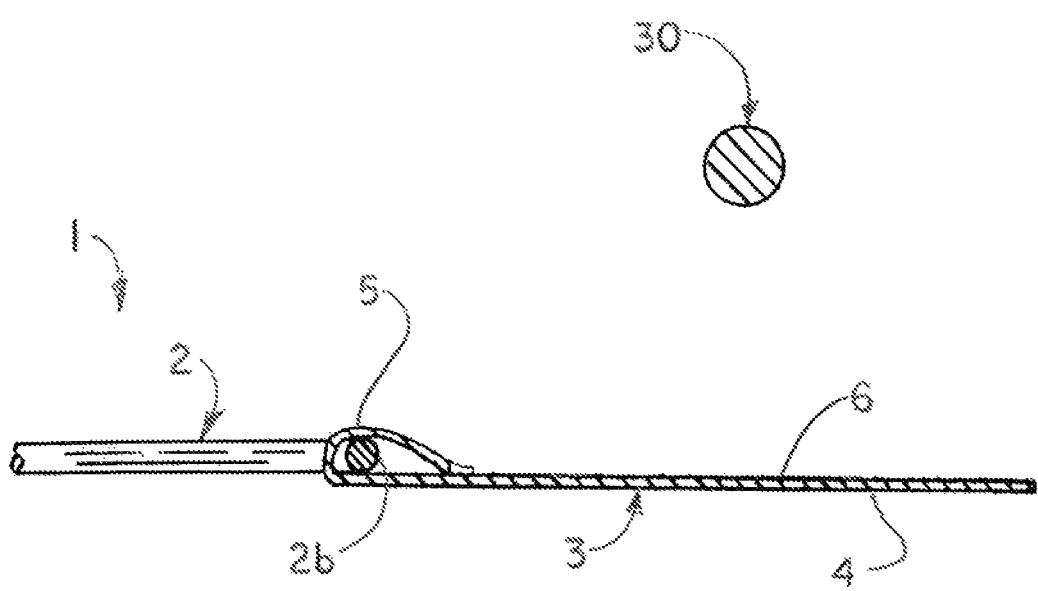
FIG. 6 is a sectional view of the line attachment member, with the cover layer removed from the adhesive surface on the base layer of the line attachment member and further illustrating typical placement of the IV line against the adhesive surface in typical attachment of the line attachment member to the IV line.
Figure 7:
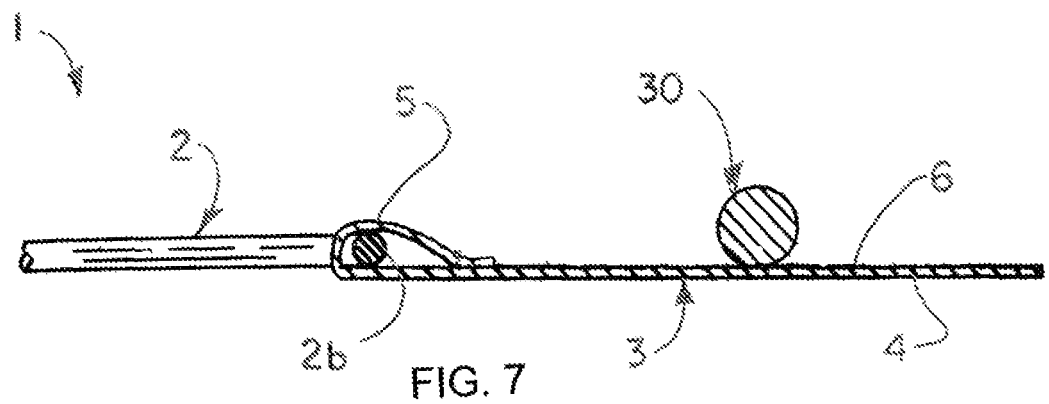
FIG. 7 is a sectional view of the line attachment member with the IV line placed against the adhesive surface in typical attachment of the line attachment member to the IV line.
Figure 8:
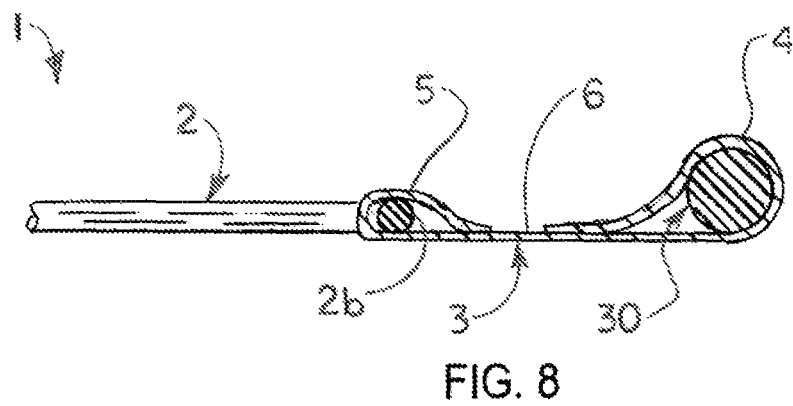
FIG. 8 is a sectional view of the line attachment member with the base layer folded over the IV line to complete attachment of the restraining member to the IV line in typical application of the illustrative IV comfort and safety assist device.

As illustrated in FIGS. 1 and 9, the IV line 30 may be pulled up toward the line attachment member 3 on the restraining member 2. As illustrated in FIGS. 6 and 7, the IV line 30 may next be placed against the adhesive surface 6 of the line attachment member 3. The base layer 4 may then be bended, folded or looped over the IV line 30 and attached to the adhesive surface 6 to complete securement of the IV line 30 to the line attachment member 3, as illustrated in FIG. 8. As further illustrated in FIGS. 1 and 9, the IV line 30 may have a descending line segment 31 which typically descends from the drip meter 26, a proximal line loop 32 which extends from the descending line segment 31, an ascending line segment 33 which extends from the proximal line loop 32, a distal line loop 34 which extends from the ascending line segment 33 and a terminal line segment 35 which extends from the distal line loop 34 and is terminated by the cannulated needle 36. Accordingly, the line attachment member 3 on the distal restraining member end 2b of the restraining member 2 may be attached to the IV line 30 at the distal line loop 34, with the distal restraining member end 2b and the proximal restraining member end 2a disposed within a common straight line. As illustrated in FIG. 1, the terminal line segment 35 of the IV line 30 may gradually slope or descend from the distal line loop 34 at the line attachment member 3 of the device 1 to the cannulated needle 36 at the arm 45 of the patient 44. The device 1 thus prevents the terminal line segment 35 of the IV line 30 from contacting the floor next to the patient bed 40 and inadvertently being crimped or stepped on, kicked or moved by medical personnel or by persons who visit the patient 44. The device 1 additionally prevents the terminal line segment 35 of the IV line 30 from becoming inadvertently caught in the bed covers, railings or other portions of the patient's bed 40 and otherwise interfering with movement and comfort of the patient 44 in the patient bed 40.

Figure 10:
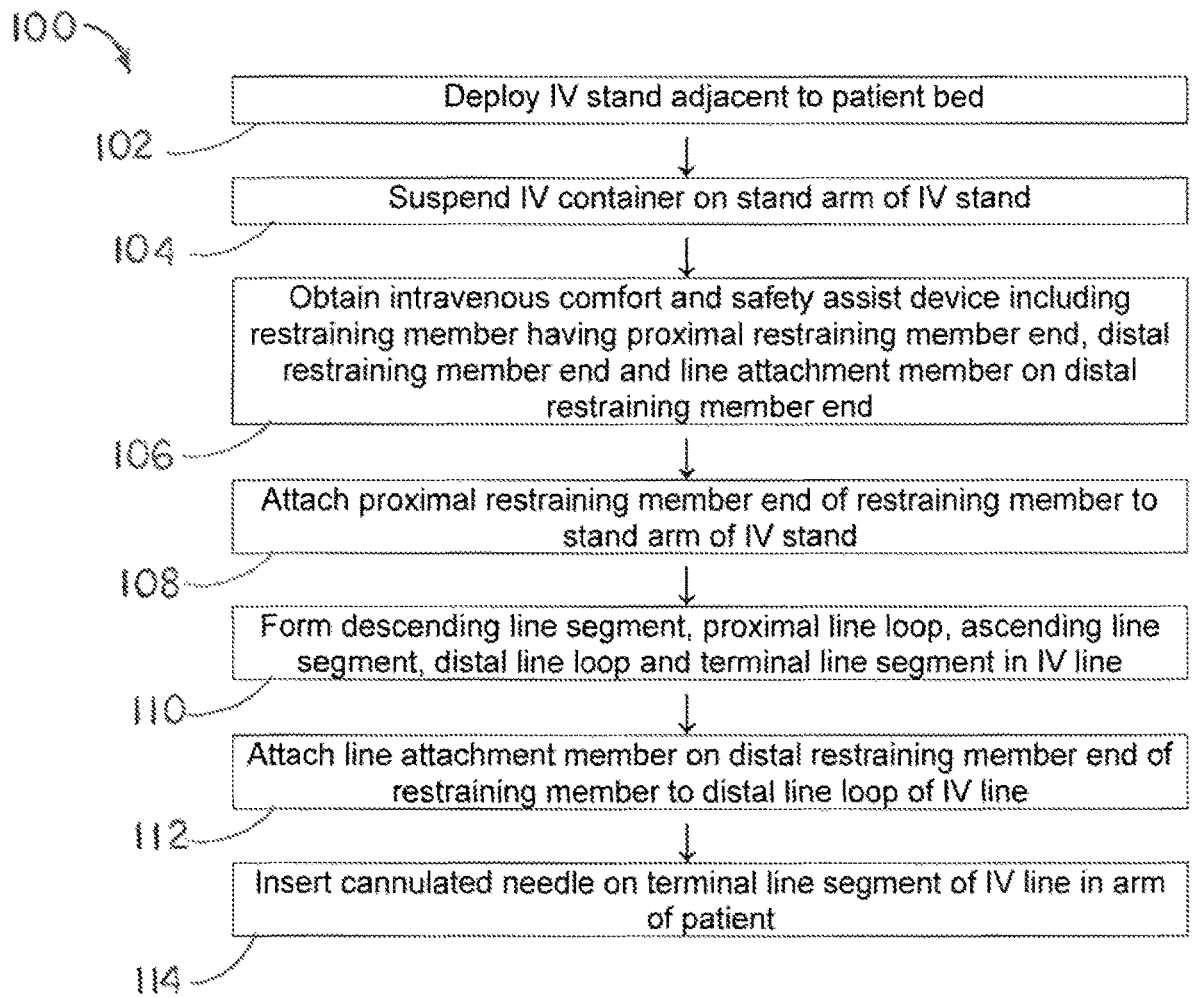
FIG. 10 is a flow diagram of an illustrative embodiment of the IV comfort and safety assist method.

Referring next to FIG. 10 of the drawings, a flow diagram of an illustrative embodiment of the IV comfort and safety assist method is generally indicated by reference numeral 100. At Step 102, an IV stand may be deployed adjacent to a patient bed.

At Step 104, an IV container may be suspended from a stand arm of the IV stand.

At Step 106, an intravenous comfort and safety assist device may be obtained. The intravenous comfort and safety assist device may include a restraining member. The restraining member may have a proximal restraining member end, a distal restraining member end and a line attachment member on the distal restraining member end. In some embodiments, the intravenous comfort and safety assist device may consist essentially of the restraining member and the line attachment member.

At Step 108, the proximal restraining member end of the restraining member may be attached to the stand arm of the IV stand typically adjacent to the IV container.

At Step 110, a descending line segment, a proximal line loop, an ascending line segment, a distal line loop and a terminal line segment may be formed in the IV line.

At Step 112, the line attachment member on the distal restraining member end of the restraining member may be attached to the distal line loop of the IV line with the distal restraining member end and the proximal restraining member end of the restraining member disposed within a common straight line.

At Step 114, a cannulated needle on the end of the terminal line segment of the IV line may be inserted in the arm of the patient typically as the patient reclines in the patient bed.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. An intravenous fluid administration comfort and safety assist method, comprising:
   deploying an intravenous fluid administration stand adjacent to a patient bed, the intravenous fluid administration stand including a stand shaft and an upper traverse supported by the stand shaft;
   suspending an intravenous fluid administration container on the upper traverse of the intravenous fluid administration stand, the intravenous fluid administration container having an intravenous fluid administration line;
   obtaining an intravenous fluid administration comfort and safety assist device including a restraining member having a proximal restraining member end, a distal restraining member end and a line attachment member on the distal restraining member end, the distal restraining member end and the proximal restraining member end disposed within a common straight line;
   attaching the proximal restraining member end of the restraining member directly to the upper traverse of the intravenous fluid administration stand adjacent to the intravenous fluid administration container;
   attaching the line attachment member on the distal restraining member end of the restraining member to the intravenous fluid administration line; and
   inserting the intravenous fluid administration line in a patient.

2. The intravenous fluid administration comfort and safety assist method of claim 1 wherein obtaining the intravenous fluid administration comfort and safety assist device including the restraining member comprises obtaining an elastic or resilient restraining member.

3. The intravenous fluid administration comfort and safety assist method of claim 1 wherein obtaining the intravenous fluid administration comfort and safety assist device including the restraining member comprises obtaining the restraining member including a band.

4. The intravenous fluid administration comfort and safety assist method of claim 3 wherein obtaining the restraining member including the band comprises obtaining the restraining member having an elastic or resilient band.

5. The intravenous fluid administration comfort and safety assist method of claim 1 wherein obtaining the intravenous fluid administration comfort and safety assist device including the restraining member having the line attachment member on the distal restraining member end comprises obtaining the restraining member having a base layer attached to the distal restraining member end, and wherein attaching the line attachment member on the distal restraining member end of the restraining member to the intravenous fluid administration line comprises forming and securing the base layer into a base layer loop extending around the intravenous fluid administration line.

6. An intravenous fluid administration comfort and safety assist method, comprising:
 deploying an intravenous fluid administration stand adjacent to a patient bed, the intravenous fluid administration stand including a stand shaft and an upper traverse supported by the stand shaft;
 suspending an intravenous fluid administration container on the upper traverse of the intravenous fluid administration stand, the intravenous fluid administration container having an intravenous fluid administration line;
 obtaining an intravenous fluid administration comfort and safety assist device including a restraining member having a proximal restraining member end, a distal restraining member end and a line attachment member on the distal restraining member end, the distal restraining member end and the proximal restraining member end disposed within a common straight line;
 attaching the proximal restraining member end of the restraining member directly to the upper traverse of the intravenous fluid administration stand adjacent to the intravenous fluid administration container;
 forming a descending line segment, a proximal line loop extending from the descending line segment, an ascending line segment extending from the proximal line loop, a distal line loop extending from the ascending line segment and a terminal line segment extending from the distal line loop in the intravenous fluid administration line;
 attaching the line attachment member on the distal restraining member end of the restraining member to the distal line loop of the intravenous fluid administration line; and
 inserting the terminal line segment of the intravenous fluid administration line in a patient.

7. The intravenous fluid administration comfort and safety assist method of claim 6 wherein obtaining the intravenous fluid administration comfort and safety assist device including the restraining member comprises obtaining an elastic or resilient restraining member.

8. The intravenous fluid administration comfort and safety assist method of claim 6 wherein obtaining the intravenous fluid administration comfort and safety assist device including the restraining member comprises obtaining the restraining member including a band.

9. The intravenous fluid administration comfort and safety assist method of claim 8 wherein obtaining the restraining member including the band comprises obtaining the restraining member having an elastic or resilient band.

10. The intravenous fluid administration comfort and safety assist method of claim 6 wherein obtaining the intravenous fluid administration comfort and safety assist device including the restraining member having the line attachment member on the distal restraining member end comprises obtaining the intravenous fluid administration comfort and safety assist device including the restraining member having a base layer attached to the distal restraining member end, and wherein attaching the line attachment member on the distal restraining member end of the restraining member to the distal line loop of the intravenous fluid administration line comprises forming and securing the base layer into a base layer loop extending around the intravenous fluid administration line.

11. An intravenous fluid administration line restraining assembly, comprising:
 an intravenous fluid administration stand including a stand shaft and an upper traverse carried by the stand shaft;
 an intravenous fluid administration container carried by the upper traverse of the intravenous fluid administration stand;
 an intravenous fluid administration line extending from the intravenous fluid administration container; and
 an intravenous fluid administration comfort and safety assist device including a restraining member having a proximal restraining member end directly attached to the upper traverse of the intravenous fluid administration stand adjacent to the intravenous fluid administration container, a distal restraining member end and a line attachment member on the distal restraining member end and attached to the intravenous fluid administration line, the distal restraining member end and the proximal restraining member end disposed within a common straight line.

12. The intravenous fluid administration line restraining assembly of claim 11 wherein the restraining member of the intravenous fluid administration comfort and safety assist device is elastic or resilient.

13. The intravenous fluid administration line restraining assembly of claim 11 wherein the restraining member comprises a band.

14. The intravenous fluid administration line restraining assembly of claim 13 wherein the band is elastic or resilient.

15. The intravenous fluid administration line restraining assembly of claim 11 wherein the line attachment member of the intravenous fluid administration comfort and safety assist device comprises a base layer attached to the distal restraining member end of the restraining member and looped and secured around the intravenous fluid administration line.

16. The intravenous fluid administration line restraining assembly of claim 15 wherein the base layer comprises a resilient pad.

17. The intravenous fluid administration line restraining assembly of claim 16 wherein the restraining member is elastic or resilient.

18. The intravenous fluid administration line restraining assembly of claim 16 wherein the restraining member comprises a band.

19. The intravenous fluid administration line restraining assembly of claim 18 wherein the band is elastic or resilient.

20. The intravenous fluid administration line restraining assembly of claim 11 wherein the intravenous fluid administration line comprises a descending line segment descending from the intravenous fluid administration container, a proximal line loop extending from the descending line segment, an ascending line segment extending from the proximal line loop, a distal line loop extending from the ascending line segment and a terminal line segment extending from the distal line loop, and the line attachment member of the intravenous fluid administration comfort and safety assist device is attached to the distal line loop of the intravenous fluid administration line.

\* \* \* \* \*